(12) United States Patent
Suehara et al.

(10) Patent No.: US 11,406,302 B2
(45) Date of Patent: Aug. 9, 2022

(54) OXYGEN MEASUREMENT DEVICE AND OXYGEN MEASUREMENT SYSTEM

(71) Applicant: TERUMO KABUSHIKI KAISHA, Tokyo (JP)

(72) Inventors: Satoru Suehara, Kanagawa (JP); Akihiro Takahashi, Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 111 days.

(21) Appl. No.: 16/584,979

(22) Filed: Sep. 27, 2019

(65) Prior Publication Data
US 2020/0022636 A1 Jan. 23, 2020

Related U.S. Application Data

(63) Continuation of application No. PCT/JP2018/008248, filed on Mar. 5, 2018.

(30) Foreign Application Priority Data

Mar. 30, 2017 (JP) .............................. JP2017-066646

(51) Int. Cl.
*A61B 5/20* (2006.01)
*A61B 5/01* (2006.01)
(Continued)

(52) U.S. Cl.
CPC ................ *A61B 5/202* (2013.01); *A61B 5/01* (2013.01); *A61B 5/1459* (2013.01);
(Continued)

(58) Field of Classification Search
CPC ....... A61B 5/01; A61B 5/14507; A61B 5/202; A61B 5/1459; A61B 5/208; A61B 5/6852; A61B 5/6853; A61M 25/0097
See application file for complete search history.

(56) References Cited

U.S. PATENT DOCUMENTS 5,096,671 A * 3/1992 Kane .................. A61B 5/14539
356/39
5,315,993 A * 5/1994 Alcala ................ A61B 5/14539
250/458.1
(Continued)

FOREIGN PATENT DOCUMENTS

JP        2739880 B2     3/1995
JP      2009523463 A     6/2009
WO    2016/049654 A1    3/2016

OTHER PUBLICATIONS

U.S. Appl. No. 16/584,997, filed Sep. 27, 2019, Suehara et al.
(Continued)

Primary Examiner — Daniel L Cerioni
(74) Attorney, Agent, or Firm — Buchanan Ingersoll & Rooney PC

(57) ABSTRACT

An oxygen measurement device constituting an oxygen measurement system includes a urethral catheter and an oxygen sensor main body. The urethral catheter has a shaft in which a urethral catheter lumen that enables circulation of urine flowed in via a urethral catheter port from inside a bladder is formed; and has a hub in which a urine lumen that is provided at a proximal end of the shaft and communicates with the urethral catheter lumen is formed. The oxygen sensor main body is provided on the hub in a manner capable of being brought into contact with urine circulating in the urine lumen, and detects oxygen in the urine.

12 Claims, 12 Drawing Sheets

(51) Int. Cl.
*A61B 5/145* (2006.01)
*A61B 5/1459* (2006.01)
*A61B 5/00* (2006.01)
*A61M 25/00* (2006.01)

(52) U.S. Cl.
CPC .......... *A61B 5/14507* (2013.01); *A61B 5/208* (2013.01); *A61B 5/6852* (2013.01); *A61B 5/6853* (2013.01); *A61B 5/743* (2013.01); *A61M 25/0097* (2013.01)

(56) References Cited

U.S. PATENT DOCUMENTS

| | | | | |
|---|---|---|---|---|
| 2005/0036751 | A1* | 2/2005 | Young | G02B 6/4428 385/100 |
| 2005/0113658 | A1 | 5/2005 | Jacobson et al. | |
| 2008/0103408 | A1* | 5/2008 | Denton | A61B 5/205 600/549 |
| 2009/0216097 | A1* | 8/2009 | Wilson | A61B 5/14542 600/327 |
| 2010/0114063 | A1 | 5/2010 | Recinella et al. | |
| 2010/0286559 | A1 | 11/2010 | Paz et al. | |
| 2012/0101480 | A1* | 4/2012 | Ingle | B29C 53/66 604/526 |
| 2015/0366498 | A1 | 12/2015 | Choi et al. | |
| 2016/0051796 | A1* | 2/2016 | Kanemasa | A61M 25/0009 604/95.04 |
| 2016/0183819 | A1* | 6/2016 | Burnett | A61B 5/14507 600/309 |
| 2016/0228031 | A1* | 8/2016 | Tsukada | A61B 5/202 |
| 2016/0310711 | A1* | 10/2016 | Luxon | A61M 25/0017 |
| 2017/0055906 | A1* | 3/2017 | Bremer | A61B 5/14865 |

OTHER PUBLICATIONS

An English Translation of the International Search Report (Form PCT/ISA/210) and the Written Opinion of the International Searching Authority (Form PCT/ISA/237) dated May 15, 2018, by the Japanese Patent Office in corresponding International Application No. PCT/JP2018/008248. (7 pages).

International Search Report (PCT/ISA/210) dated May 15, 2018, by the Japanese Patent Office as the International Searching Authority for International Application No. PCT/JP2018/008248.

Written Opinion (PCT/ISA/237) dated May 15, 2018, by the Japanese Patent Office as the International Searching Authority for International Application No. PCT/JP2018/008248.

Office Action (The First Office Action) dated Jan. 4, 2022, by the State Intellectual Property Office of People's Republic of China in corresponding Chinese Patent Application No. 201880022277.0 and an English Translation of the Office Action. (22 pages).

* cited by examiner

OXYGEN MEASUREMENT DEVICE AND OXYGEN MEASUREMENT SYSTEM

CROSS-REFERENCES TO RELATED APPLICATIONS

This application is a continuation of International Application No. PCT/JP2018/008248 filed on Mar. 5, 2018, which claims priority to Japanese Application No. 2017-066646 filed on Mar. 30, 2017, the entire content of both of which is incorporated herein by reference.

FIELD OF THE INVENTION

The present invention generally relates to an oxygen measurement device for detecting oxygen in urine excreted from kidneys, and an oxygen measurement system.

BACKGROUND DISCUSSION

Japanese Patent No. 2739880 discloses an example of an oxygen measurement device in which an oxygen sensor is inserted into the bladder and indwelled through the urinary tract of a urethral catheter. This oxygen measurement device is a device that detects oxygen in the epithelial wall by leading-out an oxygen sensor main body of an oxygen sensor from a urethral catheterization port formed at a distal portion of the urethral catheter, and bringing the oxygen sensor main body into contact with the epithelial wall of the bladder.

SUMMARY

Studies are being conducted to predict a state of the kidneys by measuring oxygen in urine, assuming that an oxygen status in urine reflects an oxygen status of kidney tissue. An oxygen measurement device such as disclosed in Japanese Patent No. 2739880 as described above is a device that detects oxygen in the epithelial wall of the bladder, and thus is not a device usefully applied to detect oxygen in urine.

If the above oxygen sensor is used to detect oxygen in urine, the main body of the oxygen sensor in the bladder may be exposed from the urethral catheter port of a urethral catheter so that the main body of the oxygen sensor may be displaced and come into contact with the bladder wall. In addition, because the oxygen sensor main body is detected as a noise when it is attached to the bladder wall, it is not easy to measure oxygen in urine accurately.

Furthermore, when the oxygen sensor main body is located at a site where urine remains without being excreted in the bladder, oxygen in urine excreted from the kidneys may not be reliably measured.

The oxygen measurement device and oxygen measurement system disclosed here enable accurate and reliable measurement of oxygen in fresh urine excreted from the kidneys through the bladder to the outside of the body.

The oxygen measurement device according to one aspect of the disclosure here includes a urethral catheter comprised of: a shaft in which is located a urethral catheter lumen that enables circulation of the patient's urine flowing into the urethral catheter lumen via a urethral catheter port from inside a bladder of the patient, a hub provided at a proximal end of the shaft, the hub including a urine lumen that is in communication with the urethral catheter lumen so that the patient's urine flowing in the urethral catheter lumen circulates into the urine lumen, and an oxygen sensor main body that is provided on the hub at a position causing the oxygen sensor main body to be brought into contact with urine circulating in the urine lumen and that detects oxygen in the urine.

According to such a configuration, since oxygen in the urine circulating in the urine lumen can be detected by the oxygen sensor main body, oxygen in fresh urine excreted from the kidneys to the outside of the body via the inside of the bladder can be accurately and reliably measured.

In the above-described oxygen measurement device, the hub may have a temperature sensor main body for detecting a temperature of urine circulating in the urine lumen.

According to such a configuration, the temperature of the urine detected by the temperature sensor main body can be used to correct oxygen detected by the oxygen sensor main body.

In the above-described oxygen measurement device, the oxygen sensor main body may be provided distal of the temperature sensor main body.

According to such a configuration, oxygen in more fresh urine circulating in the urine lumen can be detected.

In the above-described oxygen measurement device, the hub may have a flow rate sensor main body for detecting a flow rate of urine circulating in the urine lumen.

According to such a configuration, it is possible to easily know a volume of urination. In addition, it is possible to know whether or not urine is flowing stably.

In the above-described oxygen measurement device, the flow rate sensor main body may be proximal of the temperature sensor main body.

According to such a configuration, even in a case where the flow rate sensor main body generates heat, the temperature sensor main body can be less susceptible to the influence of the heat of the flow rate sensor main body as compared to a configuration in which the flow rate sensor main body is disposed at a more distal side than the temperature sensor main body.

In the above-described oxygen measurement device, the oxygen sensor main body may be distal of the flow rate sensor main body.

According to such a configuration, the flow rate of urine passed through the oxygen sensor main body can be detected by the flow rate sensor main body, and therefore a value of oxygen can be measured more quickly, and can be measured without being affected by the flow rate sensor main body.

In the above-described oxygen measurement device, in the hub, a port portion, through which a predetermined fluid is capable of being introduced into the urine lumen or from which urine circulating in the urine lumen is capable of being collected, may be distal of than the oxygen sensor main body.

According to such a configuration, in a case where it is possible to introduce a predetermined fluid into the urine lumen, it is possible to check whether or not the oxygen sensor main body is operating normally by introducing the fluid from the port portion, and in a case where it is possible to collect urine circulating in the urine lumen, it is possible to directly collect urine that is a measurement target.

In the above-mentioned oxygen measurement device, the hub may be made of a transparent material.

According to such a configuration, whether or not air bubbles or the like are present in the urine lumen can be visually recognized.

In the above-described oxygen measurement device, the hub includes an inflow suppressing portion that suppresses inflow of air to the oxygen sensor main body from a side proximal of the urine port, wherein the inflow suppressing portion is proximal of the oxygen sensor main body.

According to such a configuration, detection accuracy of the oxygen sensor main body can be improved.

In the above-described oxygen measurement device, the oxygen sensor main body may be provided with phosphor provided in the manner of being able to be brought into contact with urine in the urination port, and a base part on which the phosphor is provided, and which is configured to be capable of transmitting excitation light of the phosphor and fluorescence from the phosphor; and the hub may be configured such that a cable connector for holding an optical fiber that is optically connectable to the oxygen sensor main body is attachable to and detachable from the hub.

According to such a configuration, because it is not necessary to provide the optical fiber for exciting the phosphor in the oxygen measurement device to be disposable, the cost of the oxygen measurement device can be reduced.

In the above-described oxygen measurement device, the base part may include an elastic portion that is capable of being elastically deformed in a case where a distal end surface of the optical fiber is pressed in a state where the cable connector is attached to the hub.

According to such a configuration, when the hub is attached to the cable connector, the distal end surface of the optical fiber is reliably brought into contact with the oxygen sensor main body while suppressing damage by being excessively pressed against the oxygen sensor main body.

In the above-described oxygen measurement device, a gas permeation suppressing part that is made of a material having an oxygen gas permeation rate lower than that of a constituent material of the shaft may be provided at an outer peripheral side of the urethral catheter lumen in the shaft.

According to such a configuration, it is possible to suppress a change in an amount of oxygen in the urine (oxygen partial pressure) when flowing from the urethral catheter port to the urine lumen through the urethral catheter lumen. Accordingly, the oxygen in urine can be detected accurately.

An oxygen measurement system according to another aspect includes the oxygen measurement device as described above, a transmission cable that includes a cable connector that is attachable to and detachable from the hub, and a controller connected to the transmission cable and configured to calculate an oxygen partial pressure in the urine flowing in the hub based on a signal output by the oxygen sensor and transmitted through the transmission cable from the oxygen sensor.

According to the oxygen measurement device and oxygen measurement system disclosed here, oxygen in the urine circulating in the urination port can be detected by the oxygen sensor main body, so that oxygen in fresh urine excreted from the kidneys to the outside of the body via the inside of the bladder can be accurately and reliably measured.

According to another aspect, an oxygen measurement device that measures oxygen in a patient's urine comprises: an elongated urethral catheter, a hub and a sensor. The elongated urethral catheter possesses a distal portion that is positionable in a bladder of the patient and is comprised of a wall surrounding a urethral catheterization lumen that extends from a distal end of the elongated urethral catheter to a proximal end of the elongated urethral catheter. The elongated urethral catheter includes a urethral catheterization port that passes through the wall of the elongated urethral catheter and communicates with the urethral catheterization lumen to permit urine in the patient's bladder to enter the urethral catheterization lumen by way of the urethral catheterization port when the distal portion of the elongated urethral catheter is positioned in the patient's bladder. The hub is provided at the proximal end of the elongated urethral catheter and is comprised of a wall that surrounds a lumen extending throughout the hub and communicates with the urethral catheterization lumen so that the urine flowing in the urethral catheterization lumen circulates into the urine port. The sensor detects oxygen in the urine flowing in the lumen of the hub and comprises phosphor supported on a base, with the base being mounted in the wall of the hub and the phosphor being exposed to the lumen in the hub so that the urine circulating in the lumen of the hub contacts the phosphor.

DETAILED DESCRIPTION

Set forth below with reference to the accompanying drawings is a detailed description of embodiments of an oxygen measurement device and an oxygen measurement system representing examples of the inventive s oxygen measurement device and oxygen measurement system disclosed here.

An oxygen measurement system 12 according to one embodiment disclosed by way of example is for measuring an oxygen partial pressure (oxygen concentration) in urine excreted from kidneys into a bladder 140 in order to predict or ascertain the condition of the kidneys.

Figure 1:
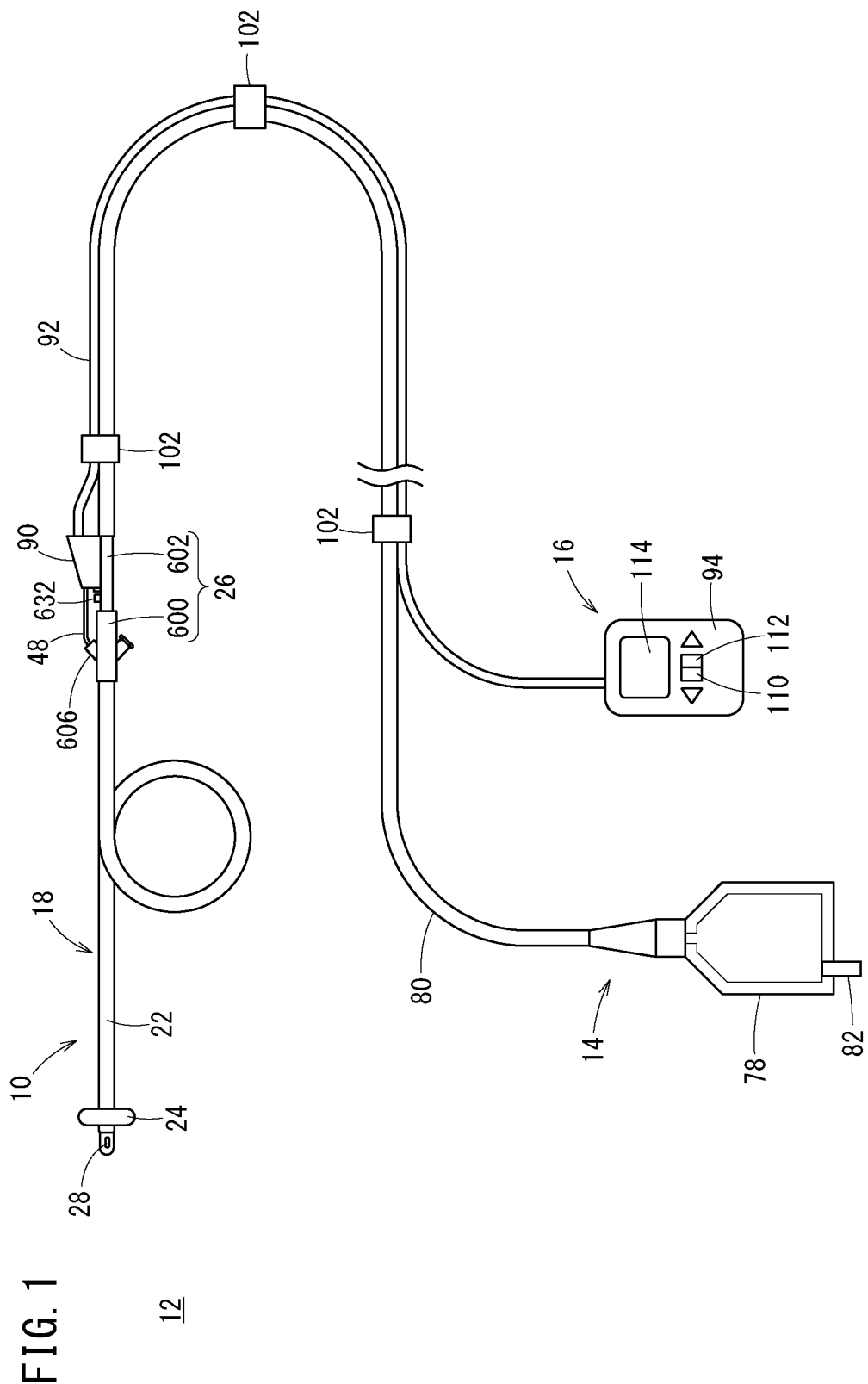
FIG. 1 is a schematic view showing a schematic configuration of an oxygen measurement system including an oxygen measurement device according to an embodiment of the present invention.
Figure 2:
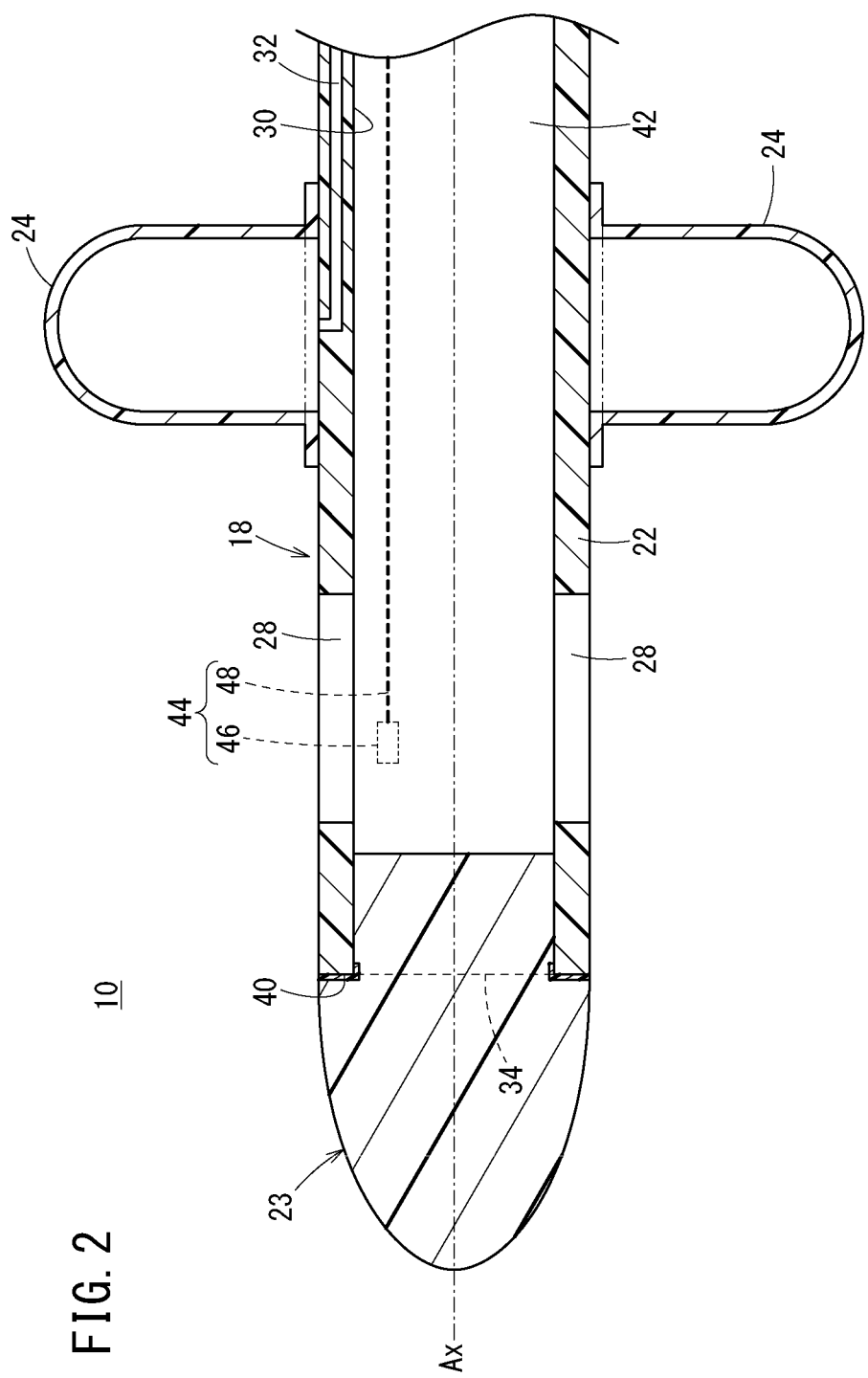
FIG. 2 is a partially omitted longitudinal cross-sectional view of a distal portion of the oxygen measurement device shown in FIG. 1.

As shown in FIG. 1, the oxygen measurement system 12 includes an oxygen measurement device 10 comprised of a urethral catheter 18, a urine collection bag 14 (a urine collection container), and a monitoring system 16. In the following description, the right side of the urethral catheter 18 in FIG. 2 is referred to as the "proximal side" (proximal end) and the left side of the urethral catheter 18 is referred to as the "distal side" (distal end). This same nomenclature applies to the other drawings.

Figure 5:
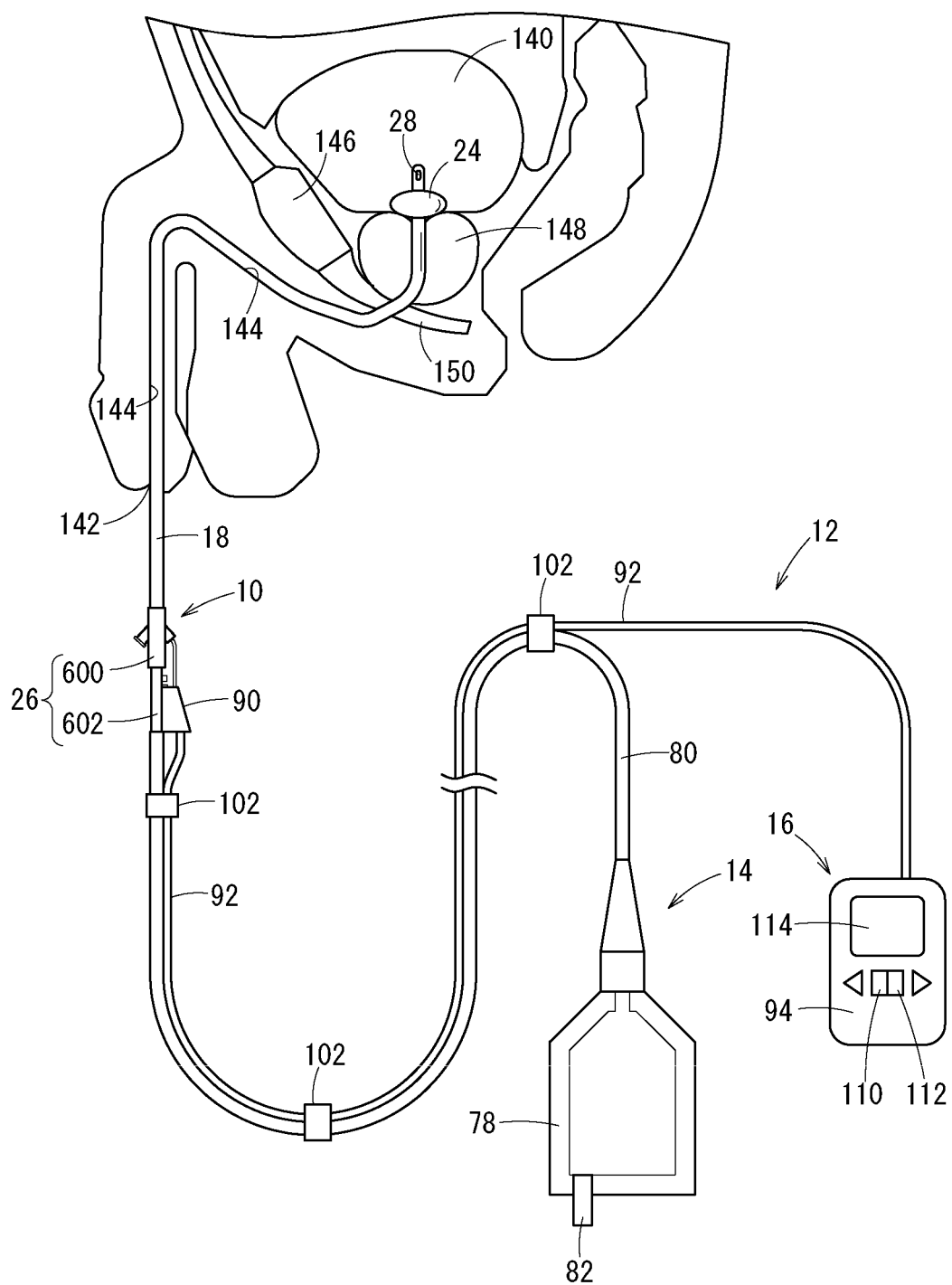
FIG. 5 is a schematic view illustrating a method for using the oxygen measurement system.

The urethral catheter 18 is a medical device that is indwelled in the living body at the time of use and directs or conveys the urine in the bladder 140 into the urine collection bag 14 disposed outside the body (refer to FIG. 5). As shown in FIGS. 1 and 2, the urethral catheter 18 includes a flexible hollow elongated shaft 22, a closing portion 23 (distal end cap) provided at the distal end of the shaft 22, a balloon 24 provided at the distal portion of the shaft 22, and a hub 26 provided at the proximal portion of the shaft 22.

The shaft 22 is a thin and long tube. The shaft 22 has adequate flexibility and adequate rigidity to allow the distal portion of the urethral catheter 18 to pass smoothly into the bladder 140 through a urethra 144 (refer to FIG. 5). Examples of constituent materials from which the shaft 22 may be fabricated include rubbers such as silicone or latex, other elastomers, vinyl chloride, polyurethane, plastic tubes, and the like.

As shown in FIG. 2, the shaft 22 includes two urethral catheter ports 28 (through holes in the wall of the shaft 22) which allow urine in the bladder 140 to flow into the shaft 22; a lumen 30 communicating with the urethral catheter ports 28 and extending the entire length of the shaft 22; and an inflation lumen 32 for circulating the inflation fluid of the balloon 24. The lumen 30 is surrounded by the wall constituting the elongated shaft 22.

Each of the urethral catheter ports 28 opens at a position that is distal of the balloon 24 on the outer peripheral surface of the shaft 22. The two urethral catheter ports 28 are provided at positions facing each other (diametrically opposed). Each of the urethral catheter ports 28 is an elongated hole extending in the longitudinal direction of the shaft 22 as generally shown in FIGS. 1 and 2. Specifically, each urethral catheter port 28 is formed in the shape (shape close to an ellipse) in which each short side of the rectangle protrudes outward in an arc shape (refer to FIG. 1). The shape, size, position and number of the urethral catheter port 28 can be optionally set.

A distal end opening portion 34 of the lumen 30 is formed at the distal end of the shaft 22. The distal end opening portion 34 of the lumen 30 is closed by the closing portion 23. The closing portion 23 may be made of the same material as the shaft 22. The closing portion 23 may be fixed to the shaft 22 by an adhesive 40.

The portion of the lumen 30 in the shaft 22 that is proximal of the closing portion 23 functions as a urethral catheter lumen or urine drainage lumen 42. The urethral catheter lumen 42 is provided such that the axis Ax of the shaft 22 is located in the urethral catheter lumen 42. According to one embodiment, the urethral catheter lumen 42 has a square cross section. However, the cross-section of the urethral catheter lumen 42 may adopt any shape.

As shown in FIG. 2, a temperature sensor 44 is embedded in the wall of the shaft 22. The temperature sensor 44 has a temperature sensor main body or sensor for detecting temperature 46 (temperature probe) for detecting the temperature in the bladder 140, and a temperature transmission unit 48 electrically connected to the temperature sensor main body 46. The temperature sensor main body 46 is at the same position as the urethral catheterization port 28 in the axial direction of the shaft 22. That is, the temperature sensor main body 46 is at the same axial position as the urethral catheter ports 28, meaning the temperature sensor main body 46 and the urethral catheter ports 28 axial overlap one another as shown in FIG. 2. The temperature sensor main body 46 includes a thermocouple, a resistance temperature detector, a thermistor, or the like. The temperature transmission unit 48 is an electric wire. The temperature sensor main body 46 may be at a position shifted from the urethral catheter port 28 in the axial direction of the shaft 22 toward the distal side or the proximal side.

The balloon 24 can be inflated and contracted (deflated) by changes in internal pressure. That is, the balloon 24 is inflated by the introduction of the inflation fluid into the balloon 24 and is contracted or deflated by the inflation fluid being discharged from the balloon 24. FIG. 1 shows the balloon 24 in the inflated state.

Figure 3:
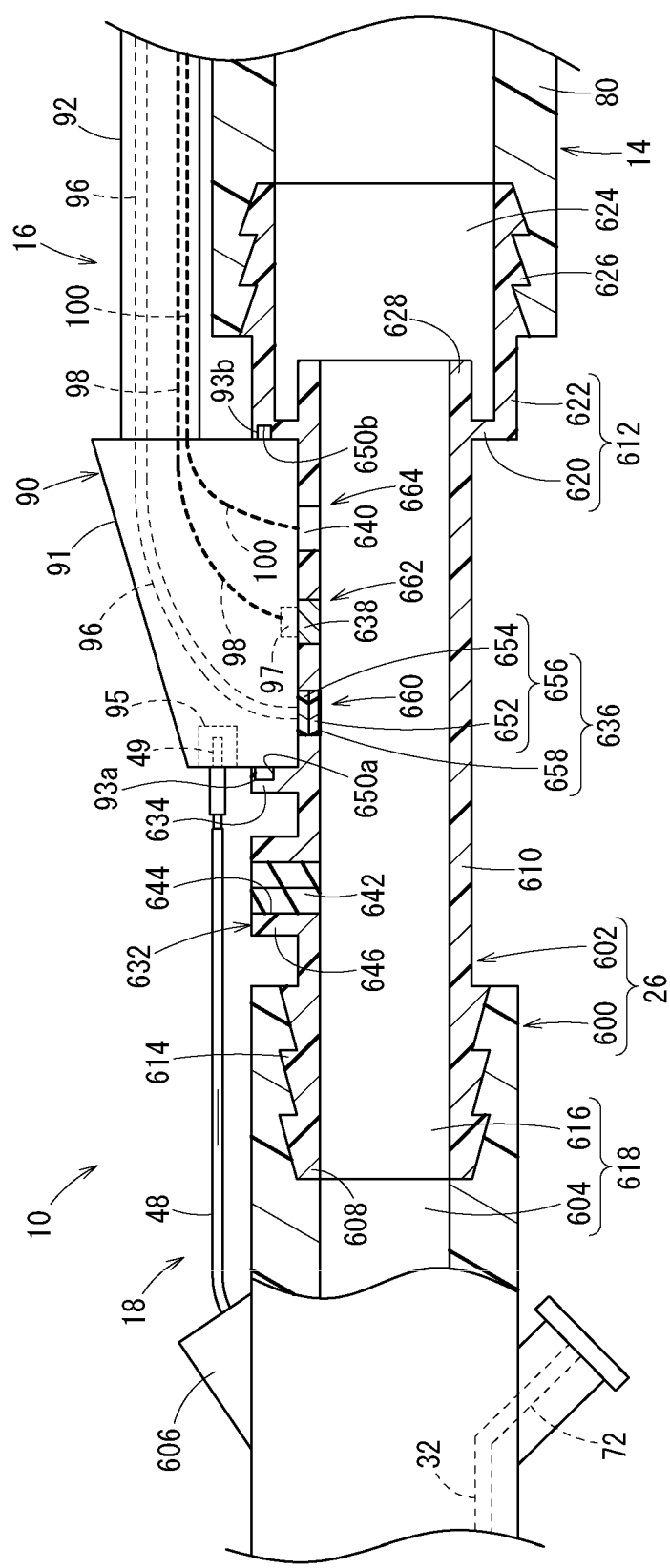
FIG. 3 is a partially omitted longitudinal cross-sectional view of a proximal portion of the oxygen measurement device shown in FIG. 1.

As shown in FIGS. 1 and 3, the hub 26 comprises a hollow hub main body 600 provided at the proximal end of the shaft 22, and a hollow interlock portion 602 provided at the proximal end of the hub main body 600. The hub main body 600 is integrally formed (monolithic structure) of a resin material or the same material as that of the shaft 22. In FIG. 3, the hub main body 600 has a first urine lumen or urine drainage lumen 604 in communication with the urethral catheterization lumen 42, a balloon inflation port 72 in communication with the inflation lumen 32, and a lead-out port 606 for leading out the proximal portion of the temperature transmission unit 48 to the outside. The balloon inflation port 72 is configured to be connectable to a pressure application device (not shown) for pumping the inflation fluid into the balloon 24 through the inflation lumen 32. The balloon inflation port 72 also includes a valve structure (not shown) that opens when the pressure application device is connected to the valve structure and closes when the pressure application device is separated from the valve structure.

The interlock portion 602 is integrally formed (monolithic structure) in a tubular shape by a resin material having transparency (transparent resin material). The interlock portion 602 includes a first connection section 608 fitted into the proximal end opening portion of the hub main body 600, an interlock portion main body 610 provided at the proximal end of the first connection section 608, and a second connection section 612 provided at the proximal portion of the interlock portion main body 610 and fitted into the distal end opening portion of a urethral catheter tube 80 of the urine collection bag 14. As shown in FIG. 3, the first connection section 608 is at the distal end of the interlock portion 602, and the second connection section 612 is at the proximal end of the interlock portion 602.

The outer surface of the first connection section 608 is in fluid tight contact with the inner surface of the proximal end opening portion of the hub main body 600 by providing a plurality of annular protrusion portions 614 on the outer surface of the first connection section 608 in the axial direction that engage similarly configured portions on the inner surface of the proximal end opening portion of the hub main body 600. A second urine lumen or urine drainage lumen 616 communicating with the first urine lumen 604 is formed in the first connection section 608 and the interlock portion main body 610. Hereinafter, the first urine lumen 604 and the second urine lumen 616 may be collectively referred to as a urine lumen or urine drainage lumen 618.

The cross-sectional shapes of the urethral catheterization lumen 42 and the urination port 618 may be identical (for example, rectangular) to each other. The flow path cross-sectional areas of the urethral catheterization lumen 42 and the urination port 618 may also be identical to each other. As a result, it is possible to suppress the occurrence of disturbance in the urine flowing from the urethral catheterization lumen 42 to the urination port 618, and therefore it is possible to circulate the urine smoothly.

The second connection section 612 includes an annular protruding portion 620 protruding outward (radially outward) from the interlock portion 602 and an extension portion 622 extending in the proximal (axial) direction from the annular protruding portion 620. The flow path cross-sectional area of the lumen 624 of the second connection section 612 is larger than the flow path cross-sectional area of the second urine lumen 616. A plurality of annular protrusion portions 626 are provided in the axial direction on the outer surface of the extension portion 622 so that the outer surface of the extension portion 622 is in fluid tight contact with the inner surface of the distal end opening portion of the urethral catheter tube 80. The proximal portion of the interlock portion main body 610 protrudes into the lumen 624 of the second connection section 612. The flow path cross-sectional area of the proximal side opening portion of a protruding portion 628 (inflow suppressing portion) which protrudes into the lumen 624 of the second connection section 612 in the interlock portion main body 610 is smaller than flow path cross-sectional area of the lumen 624 of the second connection section 612. That is, since the urine is kept in contact with the wall surface of the proximal end opening portion of the protruding portion 628 and the second urine lumen 616 serving as the lumen thereof, air is prevented from flowing into the second urine lumen 616 from the lumen 624 of the second connection section 612.

In the interlock portion main body 610, a port portion 632 for introducing a predetermined fluid into the second urine lumen 616, a support wall portion 634 located on the proximal side of the port portion 632, an oxygen sensor main body 636 for detecting oxygen in urine in the second urination port 616, a temperature sensor main body 638 for detecting the temperature of urine in the second urine lumen 616, and a flow rate sensor main body 640 for detecting the flow rate of urine in the second urine lumen 616 are provided.

The port portion 632 is provided distal of the oxygen sensor main body (sensor for detecting oxygen in urine) 636, and includes a valve body support portion 646 having a hole 644 in which a valve body 642 is disposed. The valve body 642 is formed of an elastic member such as rubber, and for example, a hollow needle body of the syringe (not shown) is configured to be able to puncture in a fluid tight manner, or a tip portion of a syringe (not shown) is configured to be fluid-tightly connectable. The port portion 632 may function as a urine collection port portion for collecting urine in the second urine lumen 616.

Fixing holes 650a and 650b for fixing a cable connector 90 of the monitoring system 16 are formed in each of a surface of the support wall portion 634 that faces the proximal direction and a surface facing the tip (distal) direction of the annular protruding portion 620. The oxygen sensor main body 636, the temperature sensor main body 638, and the flow rate sensor main body 640 are arranged in a row in this order from the distal side between the support wall portion 634 and the protruding portion 628 in a mutually separated manner. That is, the sensor that detects oxygen in urine 636, the sensor that detects urine temperature 638 and the sensor that detects urine flow rate 640 are arranged axially one after another in an axially spaced apart manner, with the sensor that detects urine temperature 638 being positioned axially between the sensor that detects oxygen in urine 636 and the sensor that detects urine flow rate 640, whereby the sensor that detects oxygen in urine 636 is distal of the sensor that detects urine temperature 638, and the sensor that detects urine flow rate 640 is proximal of the sensor that detects urine temperature 638 as shown in FIG. 3.

The oxygen sensor main body 636 is disposed proximal of the port portion 632 and distal of the temperature sensor main body 638 and the flow rate sensor main body 640, and has a base part 656 having a substrate 652 and an elastic portion 654, and a phosphor 658 provided on the base part or support 656. The phosphor 658 is applied to the surface of the substrate 652 so as to contact the urine in the second urine lumen 616. The elastic portion 654 is provided on the back surface of the substrate 652 opposite to the phosphor 658. Each of the substrate 652 and the elastic portion 654 is made of a transparent material. The substrate 652 is made of, for example, glass or polyethylene. The elastic portion 654 is made of a flexible resin material such as rubber.

The phosphor 658 is made of a material that emits fluorescence when irradiated with excitation light. Specifically, examples of the material constituting the phosphor 658 include platinum porphyrin, ruthenium complex, pyrene derivative, and the like. The phosphor 658 may be provided with a coating for blocking disturbance light. However, the phosphor 658 may not have such a coating. The phosphor 658 has a larger area than the distal end surface of an optical fiber 96 to be described later.

The temperature sensor main body 638 is provided proximal of the oxygen sensor main body 636 and distal of the flow rate sensor main body 640. In other words, the temperature sensor main body 638 is located near the oxygen sensor main body 636. The temperature sensor main body 638 is configured as a metal plate. The metal plate is preferably made of, for example, a material having a high thermal conductivity such as silver, copper, gold, stainless steel, or aluminum. In this case, a temperature of the temperature sensor main body 638 can be made substantially the same as a temperature of the urine in the second urine lumen 616. However, when the temperature sensor main body 638 can approximate a temperature of the temperature sensor main body 638 to a temperature of urine in the second urine lumen 616, the temperature sensor main body 638 may be a thin plate made from a material other than metal such as resin material. The flow rate sensor main body 640 is provided proximal of the temperature sensor main body 638, and is configured as, for example, a Karman vortex type or thermal flow rate sensor 664.

As shown in FIG. 1, the urine collection bag 14 is configured as a so-called closed bag, and includes a bag main body 78, the urethral catheter tube 80 for guiding urine in the urethral catheter 18 into the bag main body 78, and a urination or discharge portion 82 for discharging urine in the bag main body 78. Such a urine collection bag 14 is integrally formed of a resin material or the like. That is, the bag main body 78, the urethral catheter tube 80 and the discharge portion 82 may be integrally formed as one piece. However, the urine collection bag 14 may be a separate bag.

As shown in FIGS. 1 and 3, the monitoring system 16 includes the cable connector 90 attachable to and detachable from the hub 26, a long transmission cable 92 interlocked to the cable connector 90, and a monitor main body portion 94 interlocked to the transmission cable 92 (control apparatus or controller). The cable connector 90 includes a housing 91, and in the housing 91, an optical fiber 96 as an oxygen cable optically connectable to the oxygen sensor main body 636, a temperature detection unit 97 which can contact or approach the temperature sensor main body 638, a temperature cable 98 electrically connectable to the temperature detection unit 97, and a flow rate cable 100 electrically connectable to the flow rate sensor main body 640 are provided.

The cable connector 90 is attached to or detached from the hub 26 in a direction intersecting (orthogonal to) the axis of the hub 26. The housing 91 is provided with a pin 93a that can be inserted into the fixing hole 650a and a pin 93b that can be inserted into the fixing hole 650b. By operating an operation portion (not shown) provided on the housing 91, each of the pin 93a and 93b is configured to be displaceable at a lock position which protrudes outward of the housing 91 and can be inserted into each fixing hole 650a and 650b, and a withdrawing position retracted inside the housing 91 and withdrawn from the fixing holes 650a and 650b. The housing 91 is provided with a connection terminal 95 to which the terminal 49 provided at the proximal end of the temperature transmission unit 48 can be electrically connected. A cable (not shown) is electrically connected to the connection terminal 95.

The temperature cable 98 and the flow rate cable 100 are electric wires. The optical fiber 96, the temperature cable 98, and the flow rate cable 100 are bundled together by or in the transmission cable 92 and extend to the monitor main body portion 94.

As shown in FIG. 1, the transmission cable 92 is disposed along the urethral catheter tube 80, and is locked or fixed to the urethral catheter tube 80 by a plurality of latch sections 102 (banding bands). Accordingly, hindrance of the oxygen measurement device 10 by the urethral catheter tube 80 and the transmission cable 92 can be suppressed.

The oxygen sensor main body 636 and the optical fiber 96 constitute an oxygen sensor 660, the temperature sensor main body 638, the temperature detection unit 97, and the temperature cable 98 constitute a temperature sensor 662, and the flow rate sensor main body 640 and the flow rate cable 100 constitute the flow rate sensor 664.

Figure 4:
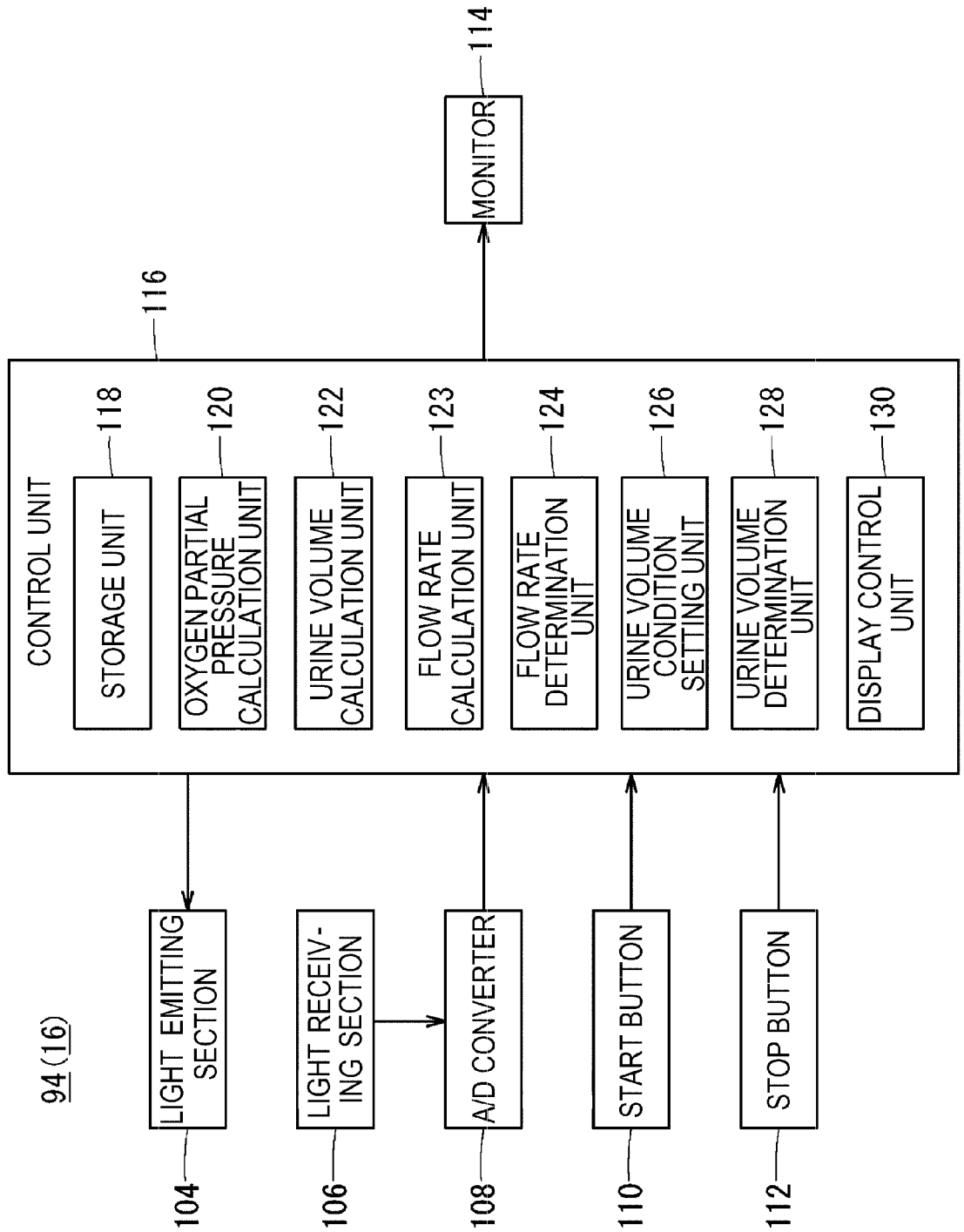
FIG. 4 is a block diagram illustrating a monitor main body portion shown in FIG. 1.

As shown in FIG. 4, the monitor main body portion 94 includes a light emitting section 104, a light receiving section 106, an A/D converter 108, a start button 110, a stop button 112, a monitor 114, and a control unit 116.

The light emitting section 104 is, for example, a light emitting diode, and emits excitation light of a predetermined wavelength to the optical fiber 96. The light receiving section 106 is, for example, a photodiode, and the fluorescence transmitted from the optical fiber 96 is incident. The A/D converter 108 converts the light reception signal of the light receiving section 106 into a digital value and outputs the digital value to the control unit 116.

The start button 110 is a button for starting measurement of an oxygen partial pressure in urine. The stop button 112 is a button for stopping measurement of the oxygen partial pressure in urine. The monitor main body portion 94 is also provided with a power button (not shown) and the like.

The monitor 114 is configured to be able to display the oxygen partial pressure in urine calculated by the control unit 116. The monitor 114 is a so-called full dot liquid crystal type display, and can display predetermined information in color. The monitor 114 has a touch panel function, and also functions as an input unit for inputting predetermined information. As an input format by the monitor 114, a pointing device such as a mouse cursor type, a touch pen type, and a touch pad type can be used in addition to the touch panel type.

The control unit 116 includes a storage unit 118 and various function implementation units. The function implementation unit is a software function unit whose function is realized by the central processing unit (CPU) executing a program stored in the storage unit 118; however, it can be realized by a hardware functional unit formed of an integrated circuit such as a Field-Programmable Gate Array (FPGA). The storage unit 118 includes a writable non-volatile memory (for example, a flash memory), and can store information input via the monitor 114, information calculated by the control unit 116, and the like.

The control unit 116 includes a storage unit 118, an oxygen partial pressure calculation unit 120, a urine volume calculation unit 122, a flow rate calculation unit 123, a flow rate determination unit 124, a urine volume condition setting unit 126, a urine volume determination unit 128, and a display control unit 130. The control unit 116 further includes a temperature input unit to which the output signal of the temperature sensor 662 is input, and a flow rate input unit (not shown) to which the output signal of the flow rate sensor 664 is input.

The oxygen partial pressure calculation unit 120 calculates the oxygen partial pressure in urine based on the output signal of the oxygen sensor 660 and the output signal of the temperature sensor 662. The urine volume calculation unit 122 calculates an amount of urine based on the output signal of the flow rate sensor 664. The flow rate calculation unit 123 calculates the flow rate V of the urine in a urinary tract 74 based on the output signal from the flow rate sensor 664. The flow rate determination unit 124 determines whether or not the flow rate V of urine calculated by the flow rate calculation unit 123 is equal to or higher than a predetermined value.

The urine volume condition setting unit 126 sets a predetermined urine volume condition. Specifically, the urine volume condition setting unit 126 sets the first urine volume determination value and the second urine volume determination value. The first urine volume determination value is calculated by multiplying, for example, a first urine volume reference value (0.5 ml/kg/h) used for determination of the first stage and second stage of acute kidney injury (AKI) by the weight of the patient. The second urine volume determination value is calculated by multiplying a second urine volume reference value (0.3 ml/kg/h) used for determination of the third stage of acute kidney injury by the weight of the patient. However, the urine volume condition setting unit 126 can set any condition. The urine volume determination unit 128 determines whether or not the urine volume calculated by the urine volume calculation unit 122 matches a predetermined urine volume condition.

The display control unit 130 changes the display format of the oxygen partial pressure displayed on the monitor 114 according to the flow rate V of urine acquired based on the output signal of the flow rate sensor 664. Specifically, the display control unit 130 displays the oxygen partial pressure on the monitor 114 in the first display format in a case where the flow rate determination unit 124 determines that the flow rate V of urine is equal to or higher than a predetermined value, and displays the oxygen partial pressure on the monitor 114 in a second display format different from the first display format in a case where the flow rate determination unit 124 determines that the flow rate V of urine is less than a predetermined value. The display control unit 130 causes the monitor 114 to display a graph indicating temporal changes in oxygen partial pressure. When the urine volume determination unit 128 determines that the urine volume corresponds to the urine volume condition, the display control unit 130 causes the monitor 114 to display a message indicating the result.

A use of the oxygen measurement device 10 will now be described.

Figure 6:
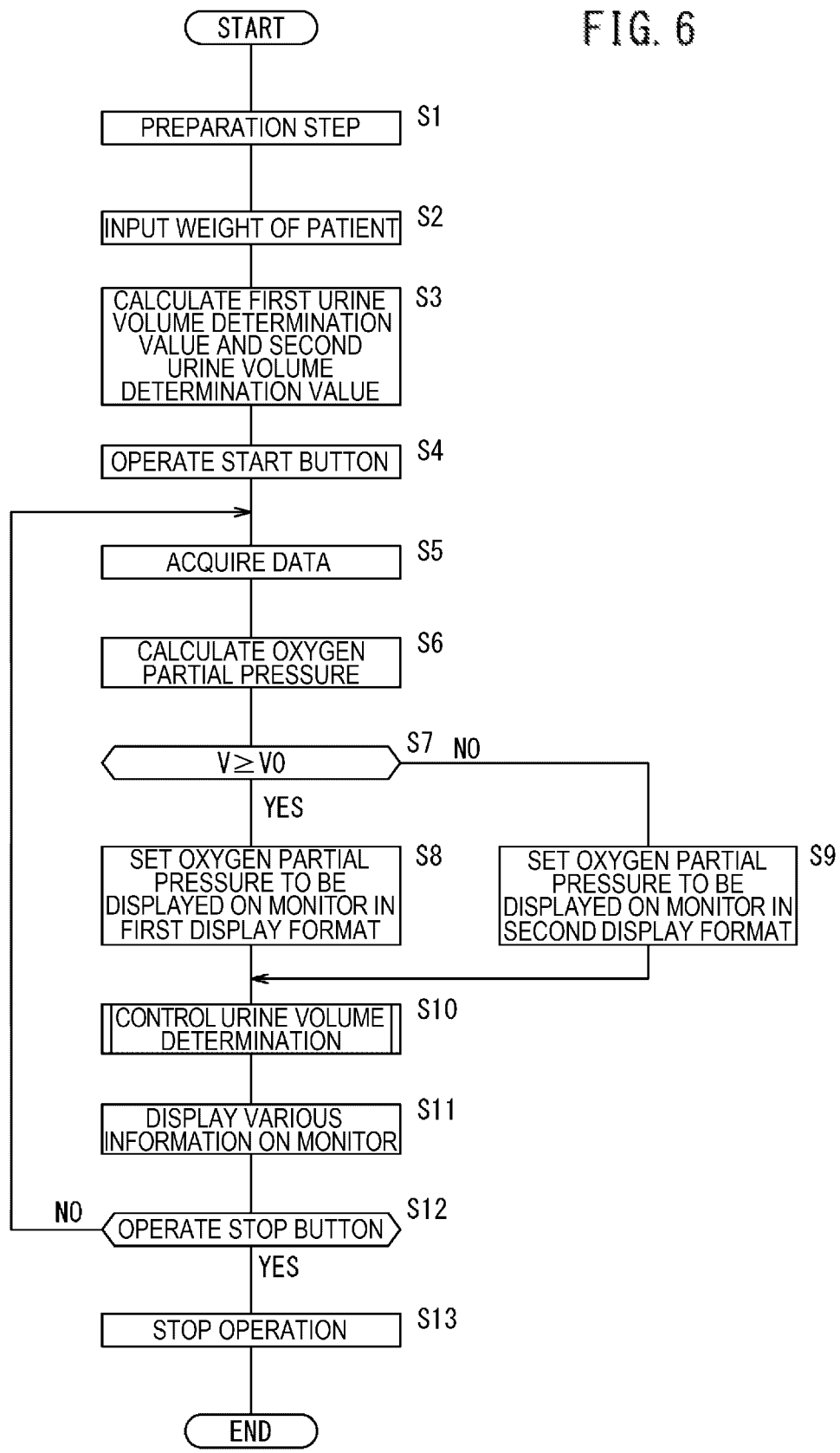
FIG. 6 is a first flow chart illustrating the method for using the oxygen measurement system.

As shown in FIGS. 5 and 6, first, the preparation process is performed (step S1 in FIG. 6). In the preparation step, the tip of the urethral catheter 18 is indwelled in the bladder 140. Specifically, the distal end of the shaft 22 coated with lubricating jelly is inserted into the urethra 144 from the urethral orifice 142 of the patient, and the urethral catheter port 28 and the balloon 24 are placed in the bladder 140. The urethral catheter 18 may be easily inserted into the bladder 140 by inserting a stylet (not shown) into the urethral catheterization lumen 42 in the shaft 22 to impart sufficient rigidity to the shaft 22.

Thereafter, the balloon 24 is inflated by pumping the inflation fluid from a pressure application device (not shown) from the balloon inflation port 72 (refer to FIG. 3) to the inflation lumen 32 (refer to FIG. 2). As a result, the urethral catheter 18 is prevented from coming out of the body, and a portion of the shaft 22 that is distal with respect to the balloon 24 and the balloon 24 is indwelled in the bladder 140. Reference numeral 146 in FIG. 5 is a pubic bone, reference numeral 148 is a prostate, and reference numeral 150 is an external urinary sphincter.

When the distal portion of the urethral catheter 18 is indwelled in the bladder 140, the urine in the bladder 140 can be excreted via the urethral catheter 18 into the urine collection bag 14. At this time, in the urethral catheter 18, urine in the bladder 140 flows into the urethral catheterization lumen 42 from the urethral catheter port 28.

In addition, as shown in FIG. 6, the user inputs the weight of the patient into the monitor main body portion 94 (step S2). Then, the urine volume condition setting unit 126 calculates the first urine volume determination value and the second urine volume determination value based on the input patient weight (step S3).

Thereafter, the user operates the start button 110 (step S4). Accordingly, measurement of the oxygen partial pressure in urine is started. When the start button 110 is operated, measurement of the oxygen partial pressure in urine is performed continuously or intermittently (for example, every 5 minutes) until the stop button 112 is operated.

Specifically, the control unit 116 acquires various data (step S5). In other words, the control unit 116 acquires the output signal of the temperature sensor 662 and the output signal of the flow rate sensor 664. Furthermore, the control unit 116 controls the light emitting section 104 to emit light of a predetermined wavelength. Then, the excitation light emitted from the light emitting section 104 is transmitted to the optical fiber 96, and the phosphor 658 of the oxygen sensor main body 636 is irradiated therewith from the distal end surface thereof. The phosphor 658 irradiated with light transitions from the ground state to the excited state, and returns to the ground state while emitting fluorescence. At this time, when oxygen molecules exist around the phosphor 658, the interaction deprives the excitation energy to oxygen molecules, and the intensity of fluorescence emission decreases. This phenomenon is called a quenching phenomenon, and the intensity of fluorescence emission is inversely proportional to an oxygen molecule concentration. The fluorescence of the phosphor 658 is incident from the distal end surface of the optical fiber 96 and is guided to the light receiving section 106. The light reception signal of the light receiving section 106 is converted into a digital signal by the A/D converter 108 and input to the control unit 116. Accordingly, the output signal of the oxygen sensor 660 is acquired.

Thereafter, the oxygen partial pressure calculation unit 120 calculates the oxygen partial pressure in urine based on the output signal of the oxygen sensor 660 (the output signal of the A/D converter 108) and the output signal of the temperature sensor 662 (step S6). In addition, the flow rate determination unit 124 determines whether or not the flow rate V of urine acquired is equal to or higher than a predetermined value (reference flow rate V0) based on the output signal of the flow rate sensor 664 (step S7). The reference flow rate V0 is stored in advance in the storage unit 118.

When the flow rate determination unit 124 determines that the flow rate V is equal to or higher than the reference flow rate V0 (step S7: YES), the display control unit 130 performs setting so that the calculated oxygen partial pressure is displayed on the monitor 114 in the first display format (step S8). On the other hand, when the flow rate determination unit 124 determines that the flow rate V is less than the reference flow rate V0 (step S7: NO), the display control unit 130 performs setting so that the calculated oxygen partial pressure is displayed on the monitor 114 in the second display format (step S9).

Figure 7:
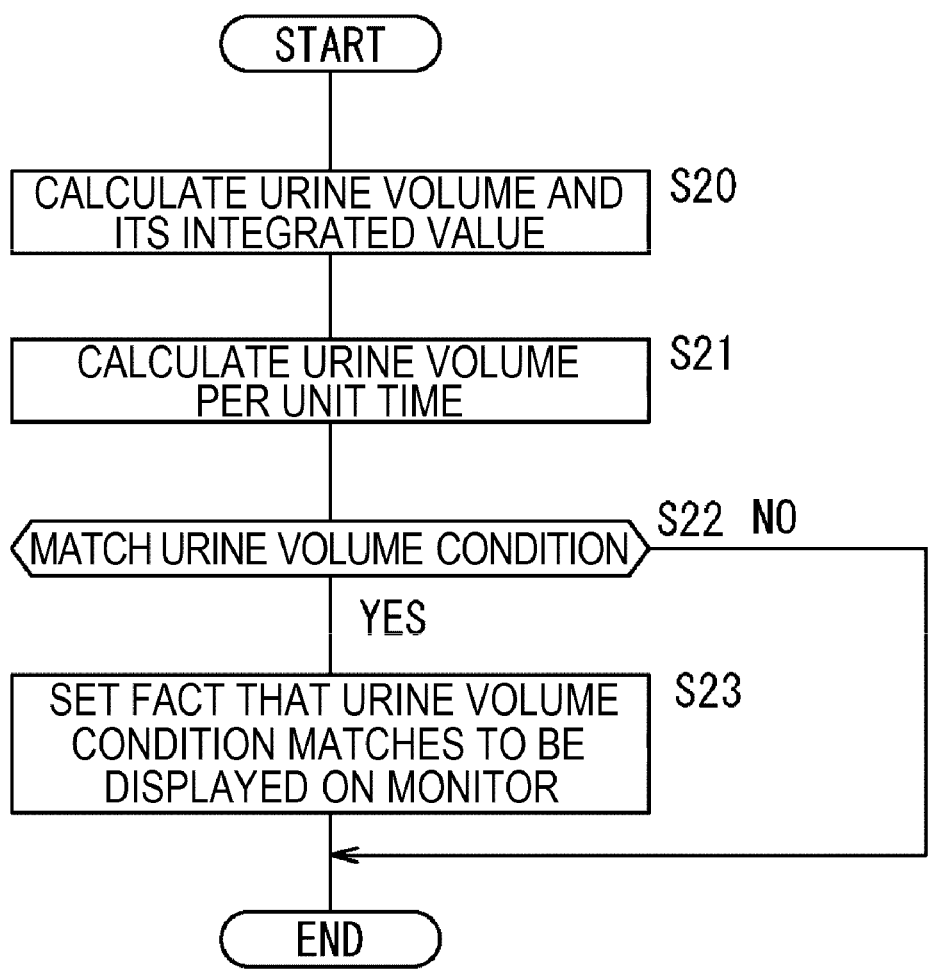
FIG. 7 is a second flow chart illustrating the method for using the oxygen measurement system.

Subsequently, urine volume determination control (step S10) is performed. In the urine volume determination control (step S10), the urine volume calculation unit 122 first calculates the urine volume and its integrated value (step S20 in FIG. 7). In other words, the urine volume calculation unit 122 calculates an amount of urine based on the output signal of the flow rate sensor 664. The calculated urine volume is stored in the storage unit 118. Then, the urine volume calculation unit 122 calculates the integrated value of the urine volume by adding the urine volume calculated in the present measurement to the urine volume stored in the storage unit 118. The integrated value of the urine volume is stored in the storage unit 118.

Thereafter, the urine volume calculation unit 122 calculates the urine volume per unit time (for example, per hour) based on the integrated value of the urine volume (step S21). Subsequently, the urine volume determination unit 128 determines whether or not the urine volume per unit time matches the urine volume condition (step S22).

Specifically, the urine volume determination unit 128 determines whether or not the urine volume per unit time corresponds to any one of the first to third stages of AKI. More specifically, the urine volume determination unit 128 determines that the urine volume per unit time corresponds to the first stage when the urine volume per unit time remains less than the first urine volume determination value for six hours or more. In addition, the urine volume determination unit 128 determines that the urine volume per unit time corresponds to the second stage when the urine volume per unit time remains less than the first urine volume determination value for 12 hours or more. Furthermore, the urine volume determination unit 128 determines that the urine volume per unit time corresponds to the third stage when the urine volume per unit time remains less than the second urine volume determination value for 24 hours or more or when no urine volume remains for 12 hours or more.

When the urine volume determination unit 128 determines that the urine volume per unit time corresponds to any one of the first to third stages of AKI (step S22: YES), the display control unit 130 causes the monitor 114 to display a message indicating that the urine volume per unit time corresponds to the urine volume condition (any one of the first to third stages) (step S23). On the other hand, when the urine volume determination unit 128 determines that the urine volume per unit time does not corresponds to any of the first to third stages of AKI (step S22: NO), the display control unit 130 causes the process to proceed to the step S11 in FIG. 6.

Figure 8:
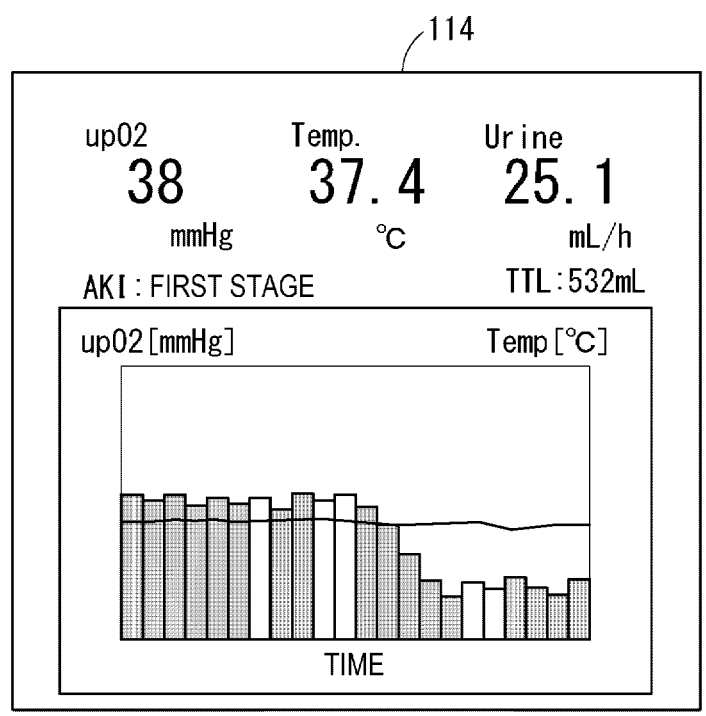
FIG. 8 is a first view showing measurement results of the oxygen measurement system which are displayed on a monitor.

Thereafter, in step S11, the display control unit 130 causes the monitor 114 to display various pieces of information. Specifically, as shown in FIG. 8, the display control unit 130 causes the monitor 114 to numerically display, for example, the oxygen partial pressure, the temperature in the bladder, the urine volume, and the integrated value of the urine volume, and causes the monitor 114 to display temporal changes in oxygen partial pressure and temporal changes in intravesical temperature in the form of a graph. In addition, when the urine volume determination control determines that it corresponds to any one of the first to third stages of AKI (step S22: YES), the display control unit 130 causes the monitor 114 to display a message indicating the result. The display control unit 130 does not cause the monitor 114 to display the AKI when the urine volume determination control determines that it does not correspond to any of the first to third stages of AKI (step S22: NO).

In the example of FIG. 8, the oxygen partial pressure of 38 mmHg, the temperature in the bladder of 37.4° C., the urine volume per unit time of 25.1 mL/h, the cumulative volume of urine of 532 mL, and AKI being the first stage are displayed. In addition, the temporal changes in oxygen partial pressure are displayed in the form of a bar graph, and the temporal changes in intravesical temperature are displayed in the form of a line graph. That is, the horizontal axis represents time, one vertical axis represents oxygen partial pressure (mmHg), and the other vertical axis represents temperature (° C.). Furthermore, in the bar graph, the filled portion is a portion displaying the oxygen partial pressure in the first display format, and the non-filled portion is a portion displaying the oxygen partial pressure in the second display format. In other words, in the bar graph, the oxygen partial pressure in the filled portion is the oxygen partial pressure in urine when the flow rate V of urine is equal to or higher than the reference flow rate V0, the oxygen partial pressure in the unfilled part is the oxygen partial pressure in urine when the flow rate V of urine is less than the reference flow rate V0.

The first display format and the second display format of the oxygen partial pressure are not limited to the example of FIG. 8. For example, in the bar graph, the first display format may be displayed in a non-filled state, and the second display format may be displayed in a filled state.

Figure 9A:
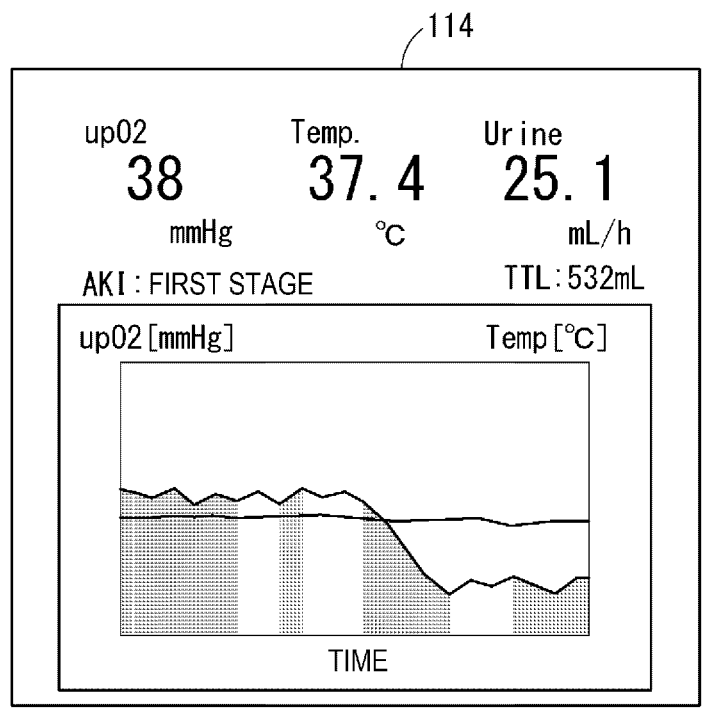
FIG. 9A is a second view showing measurement results of the oxygen measurement system which are displayed on the monitor.

In addition, as shown in FIG. 9A, the display control unit 130 may cause the monitor 114 to display a temporal change in oxygen partial pressure as a line graph. In this case, in the line graph, a thick line portion indicates the oxygen partial pressure in the first display format, and a thin line portion indicates the oxygen partial pressure in the second display format. However, the first display format may be displayed as a thin line, and the second display format may be displayed as a thick line.

Figure 9B:
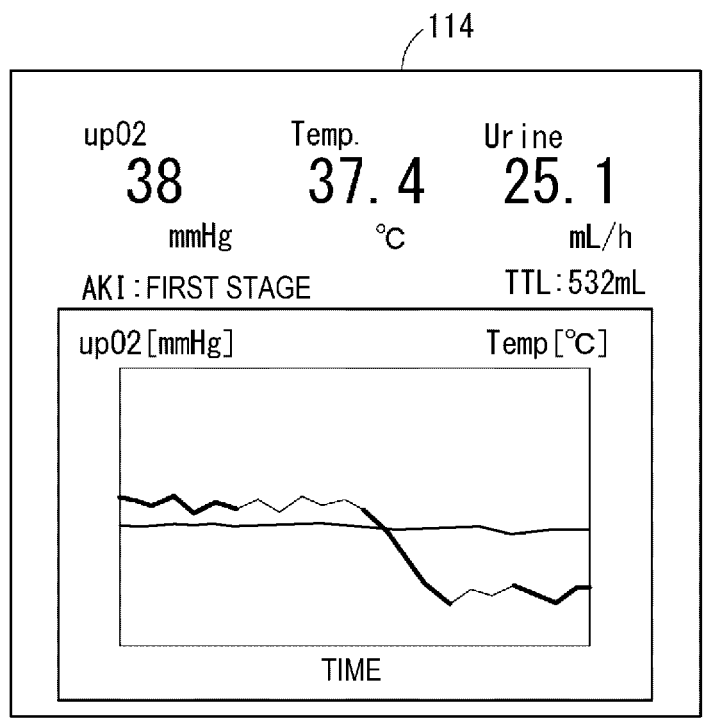
FIG. 9B is a third view showing measurement results of the oxygen measurement system which are displayed on the monitor.

In addition, as shown in FIG. 9B, in the line graph, a portion in which the lower side of the line segment indicating the value of the oxygen partial pressure is filled may be taken as the first display format of the oxygen partial pressure, and a portion in which the lower side is not filled up may be taken as the second display format of the oxygen partial pressure. However, the first display format may be displayed in a state in which the lower side is a not filled, and the second display format may be displayed in a state in which the lower side is a filled.

Thereafter, in FIG. 6, the control unit 116 determines whether or not the stop button 112 is operated (step S12). In a case where the stop button 112 has not been operated (step S12: NO), the processes after step S5 are performed. On the other hand, in a case where the stop button 112 is operated (step S12: YES), the control unit 116 stops the operation of the oxygen measurement (step S13). In other words, the light emission of the light emitting section 104 is stopped. At this stage, the oxygen measurement process of the present flowchart ends.

Next, effects of the present embodiment will be described.

The oxygen measurement device 10 includes the urethral catheter 18 and the oxygen sensor main body 636. The urethral catheter 18 has a shaft 22 in which a urethral catheterization lumen 42 that enables circulation of urine flowed in via a urethral catheter port 28 from inside a bladder 140 is formed; and has a hub 26 in which a urination port 618 that is provided at a proximal end of the shaft 22 and communicates with the urethral catheterization lumen 42 is formed. The oxygen sensor main body 636 is provided on the hub 26 in a manner capable of being brought into contact with urine circulating in the urination port 618, and detects oxygen in the urine.

As a result, oxygen in the urine circulating in the urination port 618 can be detected by the oxygen sensor main body 636, so that oxygen in fresh urine excreted from the kidneys to the outside of the body via the inside of the bladder 140 can be accurately and reliably measured.

The hub 26 is provided with the temperature sensor main body 638 for detecting the temperature of the urine circulating in the urination port 618. Accordingly, the temperature of the urine detected by the temperature sensor main body 638 can be used to correct oxygen detected by the oxygen sensor main body 636.

The oxygen sensor main body 636 is provided more distal than the temperature sensor main body 638. In this case, oxygen in more fresh urine circulating in the urination port 618 can be detected.

The hub 26 is provided with the flow rate sensor main body 640 for detecting the flow rate of the urine circulating in the urination port 618. Accordingly, it is possible to easily know a volume of urination. In addition, it is possible to know whether or not urine is flowing stably.

The flow rate sensor main body 640 is provided more proximal than the temperature sensor main body 638. Accordingly, even in a case where the flow rate sensor main body 640 generates heat, the temperature sensor main body 638 can be less susceptible to the influence of the heat of the flow rate sensor main body 640 as compared to a configuration in which the flow rate sensor main body 640 is disposed distal of the temperature sensor main body 638.

The oxygen sensor main body 636 is provided more distal than the flow rate sensor main body 640. Accordingly, the flow rate of urine passed through the oxygen sensor main body 636 can be detected by the flow rate sensor main body 640, and therefore a value of oxygen can be measured more quickly, and can be measured without being affected by the flow rate sensor main body 640.

In the hub 26, the port portion 632 through which a predetermined fluid can be introduced into the urination port 618 is provided more distal than the oxygen sensor main body 636. Accordingly, it is possible to introduce a fluid from the port portion 632, and to check whether or not the oxygen sensor main body 636 is operating normally. In addition, in a case where the port portion 632 is configured as a urine collection port capable of collecting the urine circulating in the urination port 618, urine that is a measurement target can be collected directly.

The hub 26 is made of a transparent material. Accordingly, whether or not air bubbles or the like are present in the urination port 618 can be visually recognized.

At a position proximal of the oxygen sensor main body 636 of the hub 26, the protruding portion 628 is provided as an inflow suppressing portion that suppresses the inflow of air from the proximal end of the urination port 618 to the oxygen sensor main body 636. Thereby, detection accuracy of the oxygen sensor main body 636 can be improved.

The oxygen sensor main body 636 is provided with the phosphor 658 provided in the manner of being able to be brought into contact with urine in the urination port 618, and the base part 656 on which the phosphor 658 is provided, and which is configured to be capable of transmitting excitation light of the phosphor 658 and fluorescence from the phosphor 658. The hub 26 is configured such that the cable connector 90 for holding the optical fiber 96 that is optically connectable to the oxygen sensor main body 636 is attachable to and detachable from the hub. Accordingly, because it is not necessary to provide the optical fiber 96 for exciting the phosphor 658 in the oxygen measurement device 10 to be disposable, the cost of the oxygen measurement device 10 can be reduced.

The base part 656 includes the elastic portion 654 that is capable of being elastically deformed in a case where a distal end surface of the optical fiber 96 is pressed in a state where the cable connector 90 is attached to the hub 26. Accordingly, when the hub 26 is attached to the cable connector 90, the distal end surface of the optical fiber 96 is reliably brought into contact with the oxygen sensor main body 636 while suppressing damage by being excessively pressed against the oxygen sensor main body 636.

The present invention is not limited to the configuration described above.

Figure 10A:
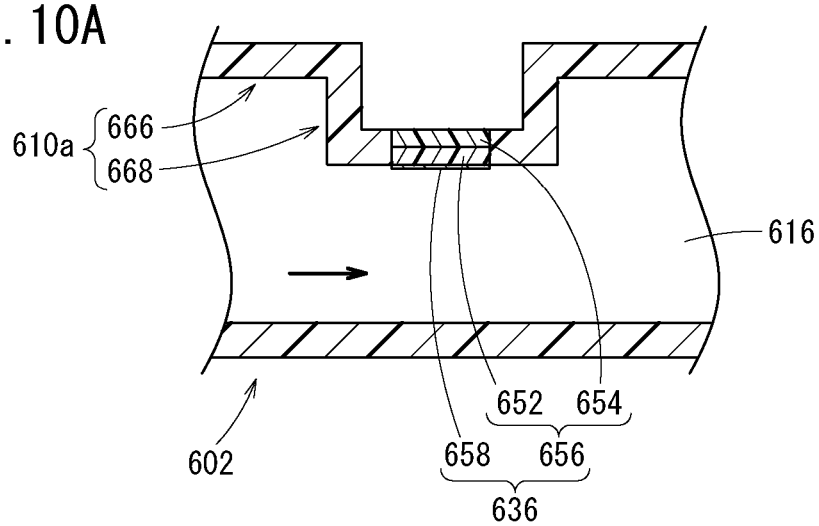
FIG. 10A is a cross-sectional view showing a modification example of an interlock portion main body.

The interlock portion 602 of the hub 26 may have an interlock portion main body 610a shown in FIG. 10A. As shown in FIG. 10A, the interlock portion main body 610a has a first portion 666 having the same flow path cross-sectional area as the flow path cross-sectional area of the first urination port 604, and a second portion 668 having a flow path cross-sectional area smaller than the flow path cross-sectional area of the first portion 666. The second portion 668 is formed to protrude inward with respect to the first portion 666. At the second portion 668, the oxygen sensor main body 636 is disposed. In this case, the urine circulating in the second urine lumen 616 can be effectively brought into contact with the phosphor 658. In addition, measurement can be more accurately performed by suppressing the inflow of air into the oxygen sensor main body 636 by the structure of the flow path cross-sectional area change portion on the proximal side; and by the flow path cross-sectional area being narrowed, and thereby improving the flow rate at the second portion 668 in a case where air gets into the flow path from the proximal side.

Figure 10B:
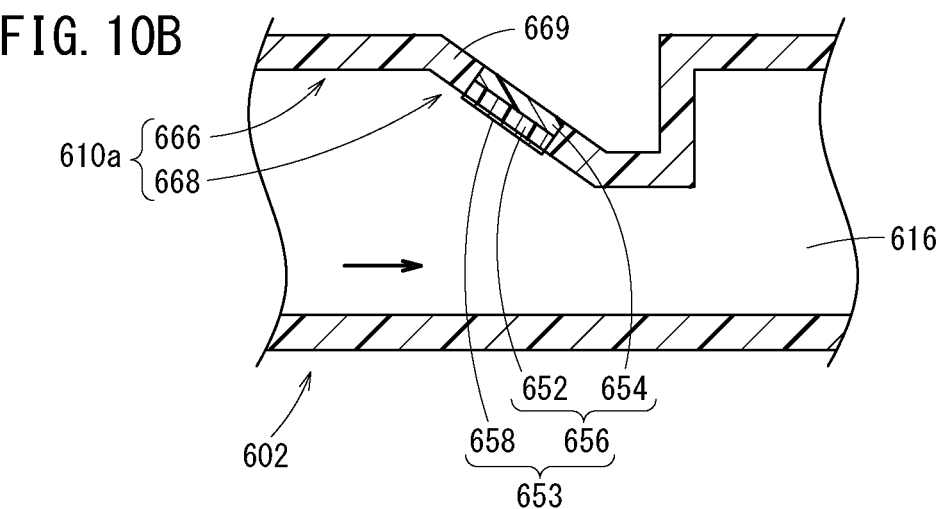
FIG. 10B is a cross-sectional view showing another modification example of the interlock portion main body.

In addition, as shown in FIG. 10B, the second portion 668 may be provided with an inclined portion 669 inclined inward toward the proximal side (right side in FIG. 10B), and the oxygen sensor main body 636 may be disposed in the inclined portion 669. In this case, the urine circulating in the second urine lumen 616 can be more effectively brought into contact with the phosphor 658. In addition, as in FIG. 10A, measurement can be performed more accurately by the change in the flow path cross-sectional area.

Figure 10C:
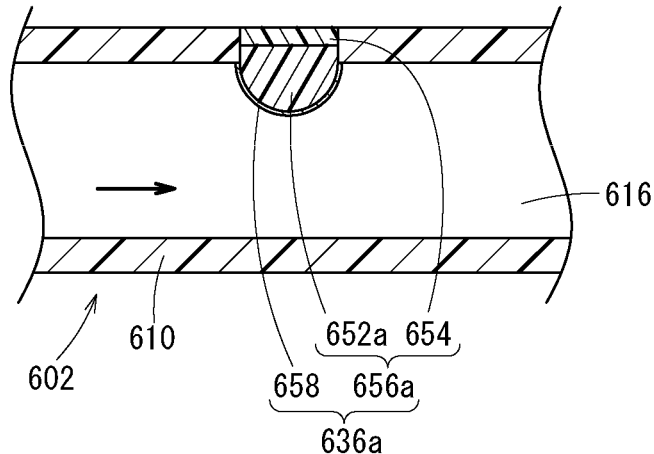
FIG. 10C is a cross-sectional view showing a modification example of an oxygen sensor main body.

The oxygen measurement device 10 may include an oxygen sensor main body 636a shown in FIG. 10C. As shown in FIG. 10C, the base part 656a of the oxygen sensor main body 636a has a substrate 652a configured to bulge inward more than the inner surface of the interlock portion main body 610. That is, the surface of the substrate 652a facing towards the second urination port 616 is positioned radially inwardly of the inner surface of the interlock portion main body 610. In addition, the phosphor 658 is applied to the outer surface of the bulging part of the substrate 652a. In this case, the urine circulating in the second urine lumen 616 can be more effectively brought into contact with the phosphor 658.

Figure 11A:
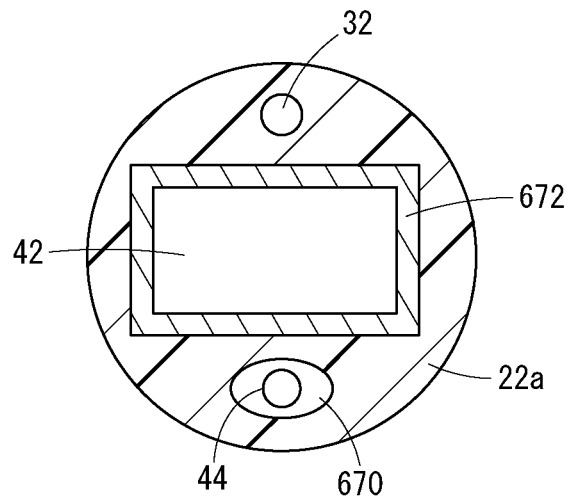
FIG. 11A is a transverse cross-sectional view of a shaft including a gas permeation suppressing part.

The oxygen measurement device 10 may include a shaft 22a shown in FIG. 11A. As shown in FIG. 11A, the shaft 22a is formed with the urethral catheterization lumen 42, the inflation lumen 32, and a sensor lumen 670 in which the temperature sensor 44 is disposed. A gas permeation suppressing part 672 (gas barrier portion) that is made of a material having an oxygen gas permeation rate lower than that of a constituent material of the shaft 22a is provided at an outer peripheral side of the urethral catheterization lumen 42 in the shaft 22a. Specifically, the gas permeation suppressing part 672 is provided on the inner surface of the urethral catheterization lumen 42 over the entire length of the urethral catheterization lumen 42.

The gas permeation suppressing part 672 is fabricated of a material having an oxygen gas permeation rate of 100 [$cm^3/m^2$·24 h·atm] or less. Specific examples of constituent materials of the gas permeation suppressing part 672 include ethylene-vinyl alcohol copolymer (EVOH), acrylonitrile copolymer, polyamide such as 6 nylon or 66 nylon, polychlorotrifluoroethylene (PCTFE), polyethylene terephthalate (PET), aluminum oxide, silica (silicon dioxide), and the like.

According to such a configuration, it is possible to suppress a change in an amount of oxygen in the urine (oxygen partial pressure) when flowing from the urethral catheter port 28 to the urination port 618 through the urethral catheterization lumen 42. Accordingly, the oxygen in urine can be detected accurately.

Figure 11B:
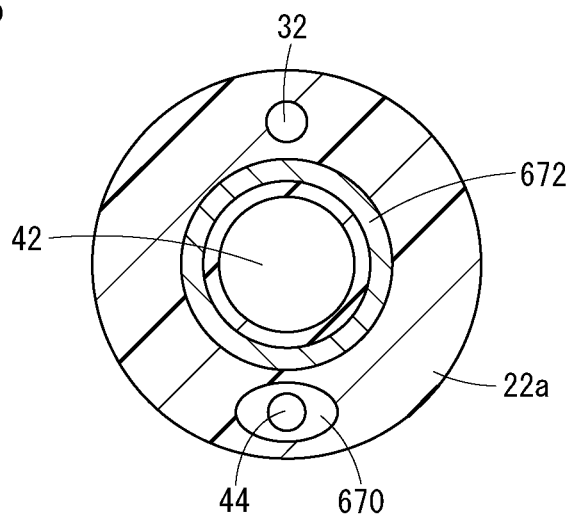
FIG. 11B is a transverse cross-sectional view showing a modification example of FIG. 11A.
Figure 11C:
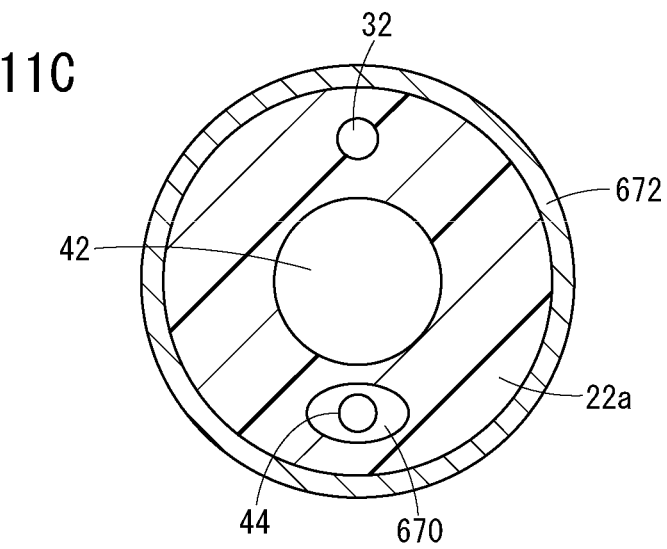
FIG. 11C is a transverse cross-sectional view showing another modification example of FIG. 11A.

The urethral catheterization lumen 42 may be embedded in the wall of the shaft 22a in the manner of covering the urethral catheterization lumen 42 from the outside (refer to FIG. 11B), or the gas permeation suppressing part 672 may be provided on the outer peripheral surface of the shaft 22a (refer to FIG. 11C).

Figure 12:
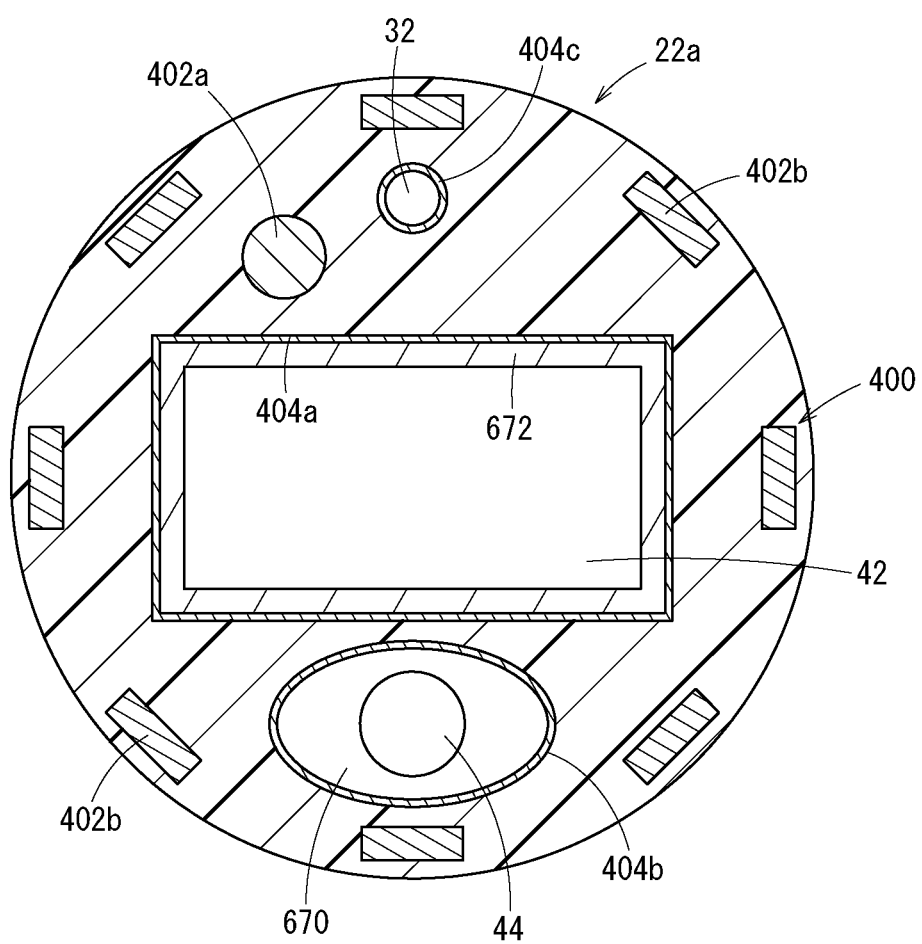
FIG. 12 is a cross-sectional view showing a configuration example of the shaft.

As shown in FIG. 12, the shaft 22a may be provided with a hard member 400 made of a material harder than that of the shaft 22a. The hard member 400 is made of, for example, metal, plastic, fiber or the like. The hard member 400 has embedded hard portions 402a and 402b embedded in the wall of the shaft 22a; a wall surface hard portion 404a provided on the wall surface constituting the urethral catheterization lumen 42; a wall surface hard portion 404b provided on the wall surface of the sensor lumen 670; and a wall surface hard portion 404c provided on the wall surface constituting the inflation lumen 32. In this case, the gas permeation suppressing part 672 is provided on the wall surface hard portion 404a. The embedded hard portions 402a and 402b extend linearly. The outer surfaces of the embedded hard portions 402a and 402b and the wall surface hard portions 404a to 404c may have asperities or may not have asperities. In addition, the embedded hard portions 402a and 402b and the wall surface hard portions 404a to 404c may be strip members in which a plurality of hole portions are formed. Furthermore, the embedded hard portions 402*a* and 402*b* may be configured in a mesh shape (net shape), or may be a braid in which fibers and the like are closely combined. According to such a configuration, it is possible to suppress damage to the gas permeation suppressing part 672 along with the expansion and contraction of the shaft 22*a*, and damage to the temperature sensor 44 in a case where the temperature sensor 44 is provided. The shaft 22*a* may be provided with at least one of the embedded hard portions 402*a* and 402*b* and the wall surface hard portions 404*a* to 404*c*.

The interlock portion main body 610 may not protrude into the lumen 624 of the second connection section 612. Even in this case, since the flow path cross-sectional area of the proximal end opening portion of the interlock portion main body 610 is larger than the flow path cross-sectional area of the lumen 624 of the second connection section 612, it is possible to suppress inflow of air from the lumen 624 of the second connection section 612 to the second urine lumen 616. That is, the configuration of a portion of the interlock portion main body 610 proximal of the oxygen sensor main body 636 functions as an inflow suppressing portion that suppresses the inflow of air from proximal the second urine lumen 616 to the oxygen sensor main body 636.

At a position proximal of the flow rate sensor main body 640 of the interlock portion main body 610, a check valve (inflow suppressing portion) that blocks the circulation of air from the proximal side to the distal side while permitting circulation of urine is provided.

The oxygen sensor main body 636, the temperature sensor main body 638, and the flow rate sensor main body 640 may be disposed to be offset from each other in a circumferential direction of the interlock portion 602. The oxygen sensor main body 636 and the temperature sensor main body 638 may be disposed to face each other with an axis line of the interlock portion main body 610 interposed therebetween.

The port portion 632 may be provided proximal of the oxygen sensor main body 636. In a case where the port portion 632 is positioned on the distal side of the oxygen sensor main body 636, when the urine of the second urine lumen 616 is collected using the port portion 632, there is a possibility of backflow of urine at a more proximal side than the oxygen sensor main body 636 to the oxygen sensor main body 636. However, in a case where the port portion 632 is provided proximal of the oxygen sensor main body 636, backflow of urine to the oxygen sensor main body 636 can be prevented.

Two temperature sensor main bodies 638 may be provided to sandwich the oxygen sensor main body 636 in an axial direction. In this case, the temperature of urine flowing through the oxygen sensor main body 636 can be detected more accurately.

The monitor main body portion 94 may be configured to be able to acquire time, atmospheric pressure around the monitor main body portion 94, humidity around the monitor main body portion 94, and temperature around the monitor main body portion 94. The time includes the current time and an elapsed time from a certain timing. The monitor main body portion 94 can be configured to be able to read and reflect a calibration value at a unique initial period (at the time of manufacture) of each sensor. Regarding a method of inputting the calibration value, it may be input by scanning a one-dimensional or two-dimensional barcode or may be input directly from an input unit. Alternatively, the calibration value may be held at a signal output unit of the urethral catheter 18 and automatically read by connecting the monitoring system 16 to the urethral catheter 18.

In the oxygen measurement system 12, operation confirmation may be performed before use. In this case, it is confirmed that an output value from each sensor of the oxygen measurement device 10 is within the normal operation range. Specifically, a reference value calculated from the temperature, humidity, and atmospheric pressure around the monitor main body portion 94 is compared with an output value from each sensor of the oxygen measurement device 10. Then, the control unit 116 of the monitor main body portion 94 determines whether or not the output value from each sensor of the oxygen measurement device 10 is within the normal range, and reports the determination results. In addition, whether or not the output value from each sensor of the oxygen measurement device 10 is within the normal range may be confirmed by acquiring the output value of each sensor using a reference solution or reference gas, and comparing the output value with the reference value.

The monitor main body portion 94 may notify various physical quantities (oxygen partial pressure, temperature in the bladder, urine volume, and the like) based on the output values from the sensors of the oxygen measurement device 10. Specifically, the monitor main body portion 94 can notify the physical quantity by a numerical value, bar graph, dial gauge, level meter, color or the like. In addition, the monitor main body portion 94 can display the transition of the physical quantity on the monitor 114 by the up and down arrows, various graphs (such as line graphs), color change progress display, and the like.

There is a time lag before changes in the bladder 140 appear as changes in urine flow rate in the oxygen measurement device 10. For this reason, the monitor main body portion 94 may display a delay time until the change in the bladder 140 appears as the output value of each sensor of the oxygen measurement device 10 on the monitor 114.

The monitor main body portion 94 allows the user to set predetermined conditions. The monitor main body portion 94 may determine and notify whether or not a state in which the setting condition is satisfied has elapsed for a set time. That is, for example, in a case where urination of the set urine volume cannot be acquired, the monitor main body portion 94 may notify when a state where setting conditions are satisfied (the low output state of the sensor, the state where the temperature in the bladder is lower than the setting temperature, and the like) continues for the set time or more.

The monitor main body portion 94 may determine and notify that the set change has occurred. That is, for example, the monitor main body portion 94 may notify when the rate of change in the flow rate of urine exceeds the set rate of change or when the range of change in the measured temperature of urine exceeds the set range of change.

The monitor main body portion 94 may have a function of maintaining the program inside, and may be configured to be able to update the program by receiving update information from the outside. In this case, the monitor main body portion 94 may receive the update information by wireless connection or wired connection (USB connection) with respect to the update information supply source. In addition, the monitor main body portion 94 may receive update information by replacing the memory card.

The monitor main body portion 94 may be configured to easily operate necessary functions. That is, the monitor main body portion 94 may be configured to have at least one physical function key and to freely assign functions to each function key. For example, the monitor main body portion 94 may be configured to be able to perform retroactive operation on past data by performing a dial operation or a slide operation of the monitor 114 (screen).

The monitor main body portion 94 may be configured to be able to print data in a selected range from an external printer or the like.

The monitor main body portion 94 may be configured to be able to divide a display area of the monitor 114 and display any data in each display area. In this case, for example, current data and past data can be easily compared. The monitor main body portion 94 may be configured to be able to output and display the display of the monitor 114 on an external display apparatus.

The monitor main body portion 94 may be configured to estimate a range of a urination volume from an infusion volume, and, at the same time, to compare the estimated range and an actual urination volume; to determine whether or not the urine volume range is within the estimated range; and to report the determination results. The infusion volume may be acquired by automatically obtaining infusion data from an infusion pump, or may be acquired by directly inputting the infusion volume.

The detailed description above describes embodiments of an oxygen measurement device and oxygen measurement system representing examples of the inventive oxygen measurement device and oxygen measurement system disclosed here. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An oxygen measurement device that measures oxygen in urine of a patient, the oxygen measurement device comprising:
    an elongated urethral catheter possessing a distal portion that is positionable in a bladder of the patient, the elongated urethral catheter being comprised of a wall surrounding a urethral catheter lumen that extends from a distal end of the elongated urethral catheter to a proximal end of the elongated urethral catheter, the elongated urethral catheter including a urethral catheter port that passes through the wall of the elongated urethral catheter and communicates with the urethral catheter lumen to permit urine in the patient's bladder to enter the urethral catheter lumen by way of the urethral catheter port when the distal portion of the elongated urethral catheter is positioned in the patient's bladder;
    a hub provided at the proximal end of the elongated urethral catheter, the hub being comprised of a wall that surrounds a lumen extending throughout the hub and communicating with the urethral catheter lumen so that the urine flowing in the urethral catheter lumen circulates into the lumen in the hub;
    an oxygen sensor main body that detects oxygen in the urine flowing in the lumen of the hub, the oxygen sensor main body being mounted in the wall of the hub and being exposed to the lumen in the hub so that the urine in the lumen of the hub contacts the oxygen sensor main body, the oxygen sensor main body comprising phosphor that emits fluorescence when irradiated with excitation light;
    a temperature sensor main body that detects temperature of the urine in the lumen of the hub, the temperature sensor main body being mounted in the wall of the hub at a position axially spaced from the oxygen sensor main body and being exposed to the lumen in the hub so that the urine in the lumen of the hub contacts the temperature sensor main body;
    a flow rate sensor main body that detects flow rate of the urine in the lumen of the hub, the flow rate sensor main body being mounted in the wall of the hub at a position axially spaced from the temperature sensor main body and being exposed to the lumen in the hub so that the urine in the lumen of the hub contacts the flow rate sensor main body;
    a cable connector comprised of: i) a housing configured to be attached to and detached from the hub; ii) an optical fiber; iii) a temperature cable separate from the optical fiber; and iv) a flow rate cable separate from the optical fiber and the temperature cable; and
    the optical fiber, the temperature cable and the flow rate cable being positioned in the housing such that when the housing is attached to the hub, the optical fiber is connected to the oxygen sensor main body, the temperature cable is connected to the temperature sensor main body and the flow rate cable is connected to the flow rate sensor main body.

2. The oxygen measurement device according to claim 1, wherein the flow rate sensor main body is proximal of the temperature sensor main body.

3. The oxygen measurement device according to claim 1, wherein the oxygen sensor main body is distal of the temperature sensor main body.

4. The oxygen measurement device according to claim 1, wherein the housing is attachable to and detachable from the hub by way of at least one pin that is positionable in a fixing hole.

5. The oxygen measurement device according to claim 1, further comprising an outwardly expandable balloon at the distal portion of the elongated urethral catheter, the expandable balloon being positioned proximal of the urethral catheter port and being in communication with an inflation lumen to introduce fluid into the balloon to outwardly expand the balloon and fix a position of the distal portion of the elongated urethral catheter in the bladder of the patient.

6. The oxygen measurement device according to claim 1, wherein the oxygen sensor main body is positioned distal of the temperature sensor main body.

7. The oxygen measurement device according to claim 1, wherein the flow rate sensor main body is positioned proximal of the temperature sensor main body.

8. The oxygen measurement device according to claim 1, wherein the hub includes a port portion configured to permit a fluid to be introduced into the lumen in the hub or to permit collection of urine circulating in the lumen in the hub, the port portion being located distal of the oxygen sensor main body.

9. The oxygen measurement device according to claim 1, wherein the hub includes an inflow suppressing portion that suppresses inflow of air to the oxygen sensor main body from a side proximal of the lumen in the hub, the inflow suppressing portion being proximal of the oxygen sensor main body.

10. The oxygen measurement device according to claim 1, wherein the oxygen sensor main body comprises a base part on which the phosphor is supported, the base part including an elastic portion that is elastically deformable when a distal end surface of the optical fiber is pressed in a state where the cable connector is attached to the hub.

11. The oxygen measurement device according to claim 1, further comprising a gas permeation suppressing part made of a material possessing an oxygen gas permeation rate lower than an oxygen gas permeation rate of a material from which the elongated urethral catheter is fabricated, the gas permeation suppressing part being positioned at an outer peripheral side of the urethral catheter lumen.

12. The oxygen measurement device according to claim 1, wherein the oxygen sensor main body comprises a base part on which the phosphor is supported, the base comprising a substrate that includes a first surface facing towards the lumen in the hub, the phosphor being applied to the first surface of the substrate, the base also comprising an elastic portion that is made of a flexible resin material and that is applied to a second surface of the substrate, the second surface of the substrate being opposite the first surface of the substrate.

* * * * *